US011051960B2

(12) United States Patent
Gerber

(10) Patent No.: US 11,051,960 B2
(45) Date of Patent: *Jul. 6, 2021

(54) CONTROL SYSTEM FOR CONTROLLING THE INFLATION OF A BALLOON IN A BALLOON STENT CATHETER SYSTEM

(71) Applicant: Elliot M. Gerber, Berwyn, PA (US)

(72) Inventor: Elliot M. Gerber, Berwyn, PA (US)

( * ) Notice: Subject to any disclaimer, the term of this patent is extended or adjusted under 35 U.S.C. 154(b) by 306 days.

This patent is subject to a terminal disclaimer.

(21) Appl. No.: 15/983,759

(22) Filed: May 18, 2018

(65) Prior Publication Data
US 2018/0263801 A1  Sep. 20, 2018

Related U.S. Application Data

(63) Continuation of application No. 13/852,818, filed on Mar. 28, 2013, now Pat. No. 9,999,530.

(60) Provisional application No. 61/618,466, filed on Mar. 30, 2012.

(51) Int. Cl.
*A61F 2/954* (2013.01)
*A61F 2/958* (2013.01)
*A61B 5/349* (2021.01)
*A61B 5/00* (2006.01)
*A61B 5/0215* (2006.01)

(52) U.S. Cl.
CPC ............. *A61F 2/954* (2013.01); *A61F 2/958* (2013.01); *A61B 5/0215* (2013.01); *A61B 5/349* (2021.01); *A61B 5/6853* (2013.01); *A61B 5/7285* (2013.01)

(58) Field of Classification Search
CPC ... A61B 5/7285; A61B 5/7284; A61B 5/7292; A61B 5/0452; A61B 5/6853; A61F 2/958; A61F 2002/9583; A61F 2/954
See application file for complete search history.

(56) References Cited

U.S. PATENT DOCUMENTS

| 4,175,264 | A | 11/1979 | Schiff |
| 5,449,344 | A | 9/1995 | Taylor et al. |
| 5,865,801 | A | 2/1999 | Houser |
| 7,250,025 | B2 | 7/2007 | Nigroni |
| 9,999,530 | B2 * | 6/2018 | Gerber .................. A61F 2/958 |
| 2005/0228359 | A1 | 10/2005 | Doyle |
| 2008/0015684 | A1 | 1/2008 | Wu |
| 2008/0221439 | A1 | 9/2008 | Iddan et al. |
| 2010/0114289 | A1 * | 5/2010 | Camus .................... A61F 2/95 623/1.11 |
| 2011/0022150 | A1 | 1/2011 | Durcan |

(Continued)

Primary Examiner — Majid Jamialahmadi
(74) Attorney, Agent, or Firm — Steven J Rocci P.C.

(57) ABSTRACT

There is disclosed a control system for controlling the inflation of a balloon in a balloon stent catheter arrangement including (i) a transducer adapted to receive a source of intracoronary arterial pressure in a patient's coronary artery and to provide arterial pressure waveform data indicative of the status of a patient's cardiac cycle based upon the intracoronary arterial pressure, (ii) a processing system adapted to process the arterial pressure waveform data, and (iii) an inflation pump adapted to inflate the balloon. The processing system is adapted to cause the inflation pump to inflate the balloon in diastole, corresponding to about 55% to about 85% of a single R-R interval of the cardiac cycle, by an amount sufficient to achieve fixation of the stent at a target site in the coronary artery.

10 Claims, 8 Drawing Sheets

(56) References Cited

U.S. PATENT DOCUMENTS

2011/0295302 A1* 12/2011 Mohl ............... A61B 17/12109
606/194
2012/0130468 A1    5/2012 Khosravi
2013/0166011 A1    6/2013 Strommer

* cited by examiner

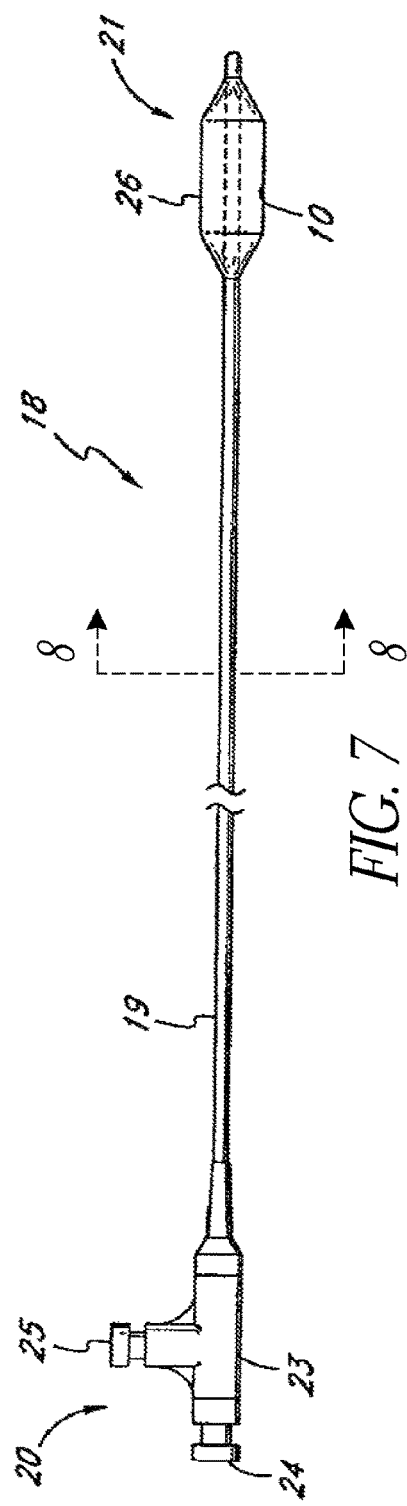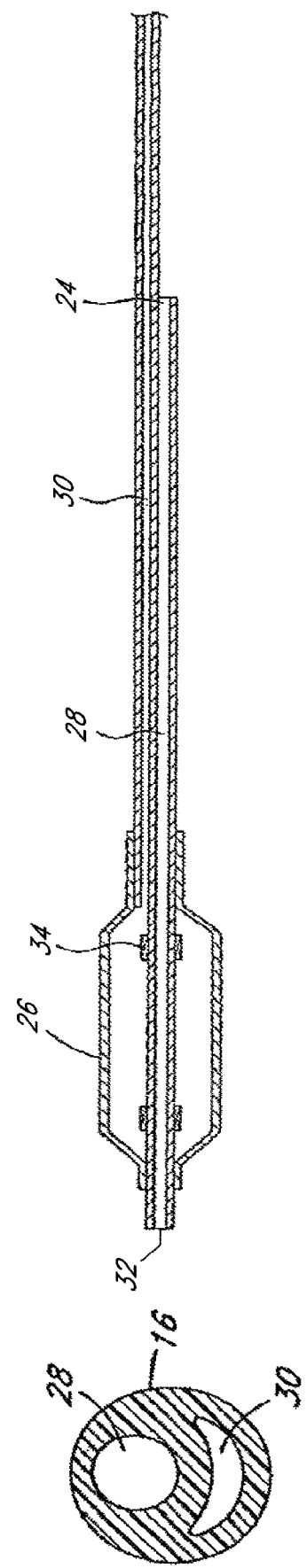

CONTROL SYSTEM FOR CONTROLLING THE INFLATION OF A BALLOON IN A BALLOON STENT CATHETER SYSTEM

CROSS REFERENCE TO RELATED APPLICATIONS

This application claims priority to and the benefit of Provisional U.S. Patent Application No. 61/618,466, filed on Mar. 30, 2012, entitled "Diastolic Coronary Stent Deployment System For Precise Bifurcation Lesion Stenting And Prevention Of Compromise To The Branch Vessel As Well As Optimal Ostial Lesion Stenting," and U.S. patent application Ser. No. 13/852,818, filed Mar. 28, 2013, entitled "Diastolic Coronary Stent Deployment System For Precise Bifurcation Lesion Stenting," the entireties of which are incorporated herein by reference.

FIELD

Disclosed is a method and device, including a control system, which deploys a coronary stent at a precise location, such as to treat bifurcation lesions. Its function is to avoid trauma to or compromise of a branch vessel when the lesion is immediately before or after a bifurcation. It is also well suited for use in ostial lesions.

BACKGROUND

As a result of movement of the coronary arteries during cardiac motion, it is difficult to accurately and precisely place and deploy a coronary stent in the location of a stenosis without compromising a branch vessel. Particularly, due to movement of the coronary arteries, the balloon of a balloon stent is likely to be inflated at an inopportune time such that it is deployed distally or proximally of the coronary lesion. Trauma and/or other complications may therefore result. The problem results because the timing of the balloon inflation is at the direction of the attending surgeon, who is determining when to inflate the balloon, and then manually inflating it. In addition, balloon inflation may take several seconds. Thus, the surgeon is not likely to time the inflation properly in accordance with diastole, and the balloon may not deploy in the desired location. The present invention addresses this shortcoming.

SUMMARY

There is provided in accordance with one aspect of the present invention a system for precise stent deployment in synchronization with the cardiac cycle. The system comprises a cable set having a first connector for connection to a source of a signal that is indicative of the status of the cardiac cycle, and a second connector for connection to a processor. The processor converts cardiac cycle data into a control signal for controlling inflation of a balloon catheter such that the balloon catheter reaches inflation at a point within the range of from about 55% to about 85% into the R-R interval. An inflation pump is provided, for inflating the balloon responsive to the control signal. A third connector is provided in communication with the inflation pump, for releasable connection to the balloon catheter. The source of a signal that is indicative of the status of the cardiac cycle may comprise a surface EKG signal, or arterial pressure waveform data.

In accordance with another aspect of the invention, there is provided a method of precise stent deployment in synchronization with the cardiac cycle, while preventing compromise to a branch vessel as well as optimizing ostial lesion stenting. The method comprises the steps of obtaining a transduced intracoronary arterial pressure curve, determining balloon inflation characteristics that will cause the balloon to reach an inflation endpoint at a predetermined point during diastole, and initiating balloon inflation in accordance with the determined inflation characteristics such that the balloon reaches inflation at the predetermined inflation endpoint. Preferably the predetermined endpoint is at a vascular bifurcation with a positional accuracy of within about +/−1 mm.

The transduced intracoronary arterial pressure curve may be obtained from a guiding catheter placed in an ostium of a coronary artery undergoing treatment. The predetermined point may be within the range of from about 55% to about 85% into the R-R interval, preferably within the range of from about 65% to about 75% into the R-R interval.

In accordance with a further aspect of the invention, there is provided a method of precise stent deployment in synchronization with the cardiac cycle. The method employs a system having a processor for generating a control signal for controlling inflation of a balloon catheter in response to a transduced intracoronary arterial pressure curve such that inflation is reached at a predetermined point during diastole, connecting the processor to a source of cardiac cycle data, connecting the balloon catheter to the system, and deploying the stent from the balloon in response to the control signal, to a site adjacent a vascular bifurcation with a positional accuracy of within about +/−1 mm. The site may be a Left Main ostial lesion, a Right Coronary ostial lesion, or other site.

The disclosed system and method allows deployment of the balloon stent within about 1 mm of the desired location by automatedly inflating the balloon during diastole, when the coronary vessel is experiencing minimal movement from cardiac motion. In contrast to the prior art, where it may take seconds to inflate the balloon, the disclosed system and method may accomplish rapid inflation or series of successive inflations lasting only milliseconds, and in synchrony with the cardiac cycle, through computer operation.

BRIEF DESCRIPTION OF THE DRAWINGS

FIG. 7 is a side elevational view of a stent deployment catheter useful in the practice of the present invention.

FIG. 8 is a cross sectional view taken along the line 8-8 of the catheter in FIG. 7.

FIG. 9 is a side elevational cross section through a distal section of a stent deployment catheter as in FIG. 7, but reconfigured for rapid exchange.

DETAILED DESCRIPTION OF THE PREFERRED EMBODIMENT

Figure 1:
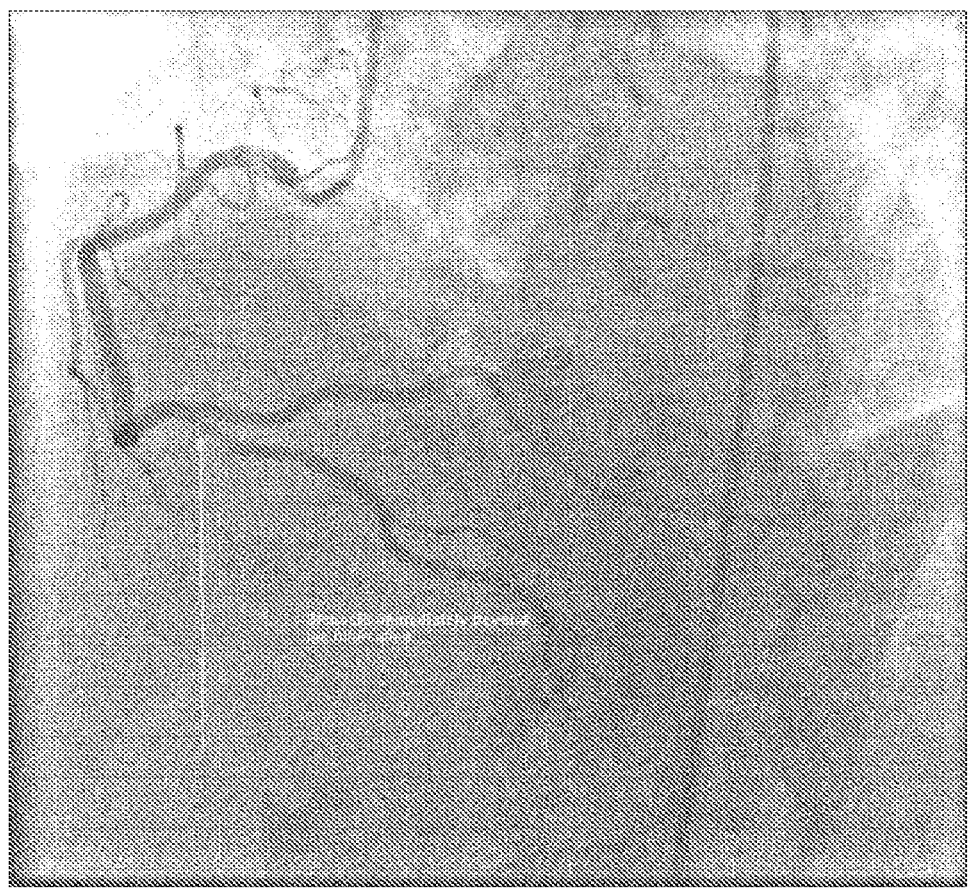
FIG. 1 is a photograph of a coronary angiogram showing an example of a coronary stenosis immediately beyond a bifurcation point.

FIG. 1 is a photograph of a coronary angiogram showing an example of a coronary stenosis immediately beyond a bifurcation point.

Figure 2:
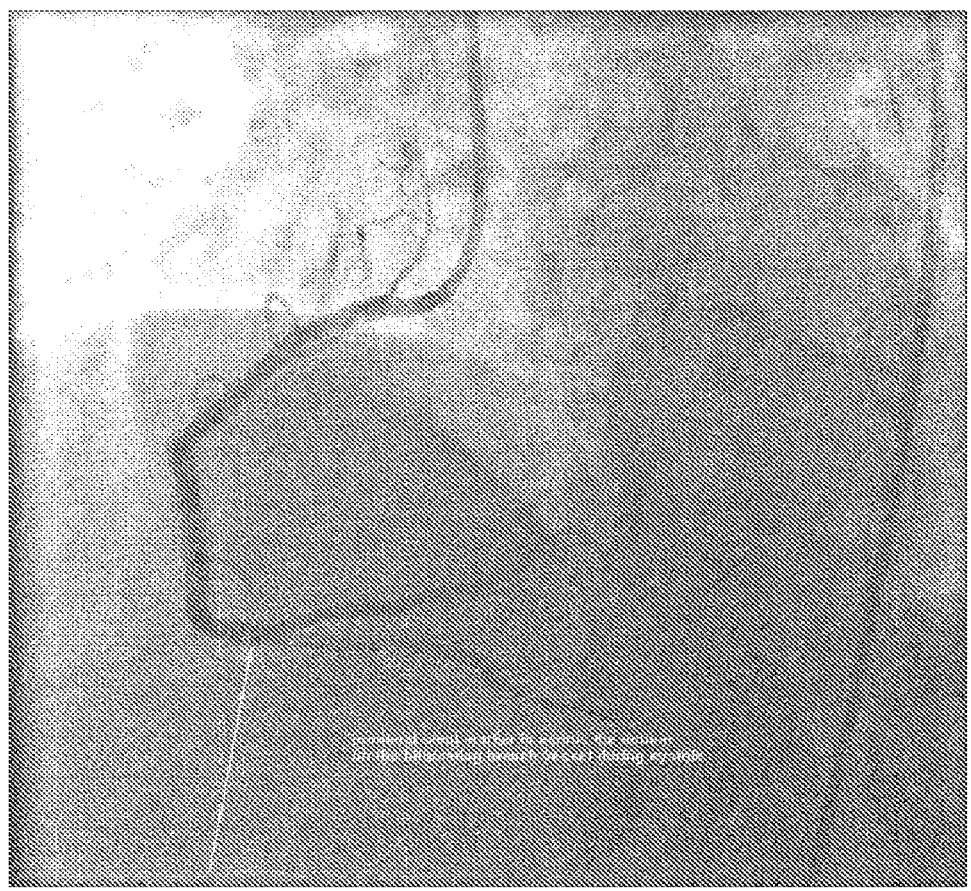
FIG. 2 is a photograph of a coronary angiogram as in FIG. 1, showing the proximal stent marker across the ostium of the bifurcating branch vessel during systole.
Figure 3:
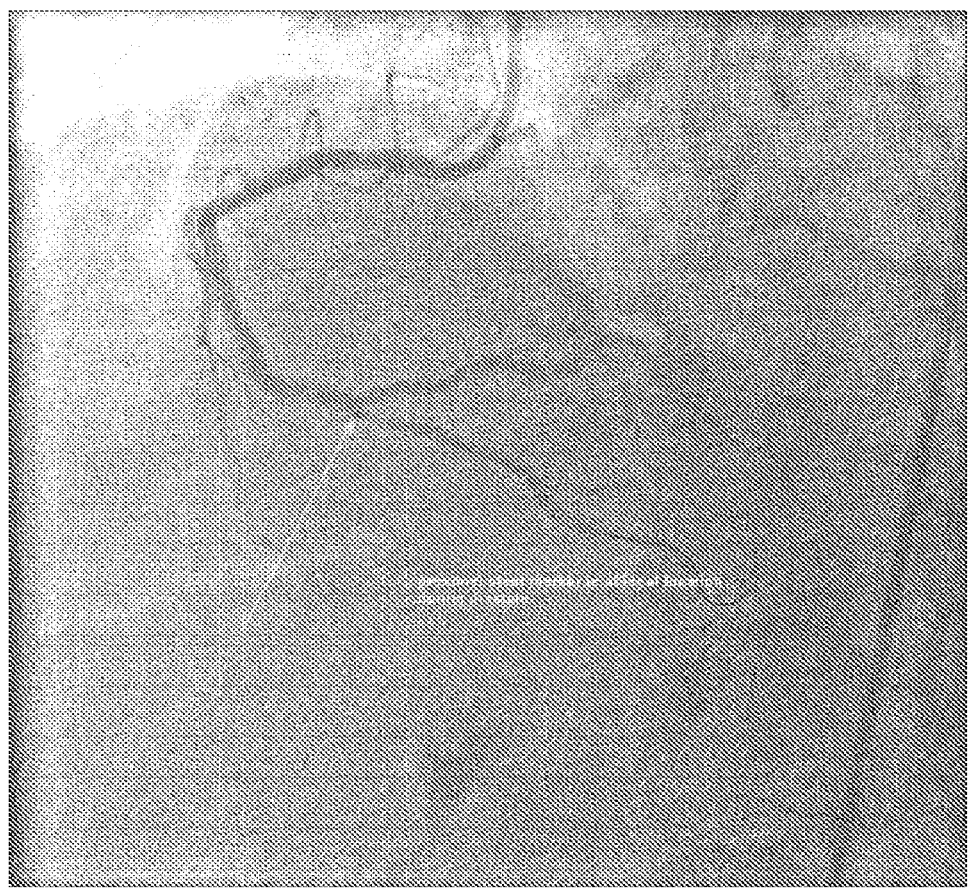
FIG. 3 is a photograph of a coronary angiogram as in FIG. 2, showing repositioning of the proximal stent marker at its ideal location during diastole.

Current technology does not allow precise deployment of a stent within about 1 mm of a desired target site due to movement of the heart and resultant relative movement of the stent to the coronary stenosis. FIG. 2 shows an undeployed stent with radiopaque markers at the proximal and distal ends of the stent. FIG. 2 shows the location of the stent during systole (myocardial contraction). FIG. 3 shows the same stent, in the same patient during diastole (myocardial relaxation), as can be seen, during the systolic phase, the stent may (undesirably) be deployed across the branch vessel resulting in its compromise. However during the diastolic phase the stent is more easily deployed in an ideal position resulting in improvement in the stenosis and no compromise of the side branch vessel.

Once the physician (operator) manually places the stent in the ideal diastolic position, the inflation system of the present invention insures deployment of the stent during diastole, thereby precisely delivering the stent to a preselected target location. There are two well accepted methods for the timing of systole and diastole and gating of these events using mechanical devices. Intra-aortic balloon pumps currently used in the patient with cardiogenic shock inflate during diastole and deflate during systole. The inflation and deflation of this large descending aortic device is synchronized to diastole using either the surface electrocardiogram or an arterial pressure waveform. Another example of a device in current use that is timed to diastole is cardiac CT angiography. Acquisition of images using cardiac computed tomography are acquired during diastole when cardiac motion essentially ceases. This serves to eliminate blurring of the cardiac CT image caused by cardiac movement.

The device described herein gates or synchronizes the diastolic deployment of the stent in a lesion at a bifurcation point, without comprising the side branch. This occurs by timing the stent deployment with the transduced intracoronary arterial pressure curve. Using intracoronary pressure is valuable to the proper intracoronary placement of this stent as there is an approximate 50 millisecond delay between coronary pressure and peripheral arterial pressure (blood pressure) as would be obtained typically in the upper or lower extremities.

Another accurate way of timing stent deployment in the diastolic phase is to gate the inflation device using an electrical measure of diastole such as timing from the T-wave on a surface EKG. Preferably, the stent deployment is timed to a specific percentage of the R-R interval on a surface EKG as is currently used in cardiac CT. A recognized potential limitation of this device is its use in a patient with a highly irregular cardiac rhythm such as atrial fibrillation.

Below is a generalized description of the system. Implementation details of the signal sensing, signal processing and driving circuitry aspects of the present invention are understood in the art. In addition, hardware components of the present system, including the stent deployment catheter, computer driven pumps and computer driven flow regulators will also be understood by those of skill in the art, such that one of skill in the art in view of the disclosure herein may construct systems for accomplishing the precise stent deployment described herein.

The system of the present invention may be adapted for use with current standard stent catheters. The transduced intracoronary arterial pressure may be obtained from the guiding catheter placed in the ostium of the coronary artery undergoing treatment. Current inflation devices use a combination of intravenous contrast solutions and water to fill the stent deployment balloon. This device may employ a liquid such as contrast combined with water to deploy the balloon but may also use a gas such as the helium or carbon dioxide such as that used in the intra-aortic counter pulsation device. Software processes diastole data from the intracoronary pressure waveform or electrical diastole and causes the stent deployment device to actuate during mechanical diastole. Since accurate deployment should occur within a matter of milliseconds, the deployment device rapidly inflates once to achieve full stent deployment or may require a series of diastolic inflations that gradually reach nominal stent size. As utilized herein, "precise deployment" means deployment of the stent within about 1 mm, and preferably within about 0.75 mm, and most preferably within about 0.5 mm of a predetermined site. For example, an end of the stent may be preferably deployed within about 0.5 mm of the ostium to a branch artery. The location of the stent relative to the ostium can be noted angiographically during diastole, and the system of the present invention utilized to insure precise deployment of the stent at the target site.

In some implementations of the invention, sufficient deployment of the stent to engage the arterial wall and retain the axial location of the stent is preferably accomplished at the target site, during the preselected phase of diastole. A central processing unit in the controller takes into account factors such as the inflation rate of the balloon under given inflation pressure circumstances, to calculate the time at which the commencement of inflation needs to occur in order to achieve fixation of the stent in the vessel at the target site. Arterial fixation may occur at the same time as complete stent deployment; however, it is contemplated that in certain environments arterial fixation of the stent may be achieved prior to complete stent deployment. Once fixation is achieved, the remainder of stent dilation may be accomplished without regard to the stage of the cardiac cycle.

Figure 4:
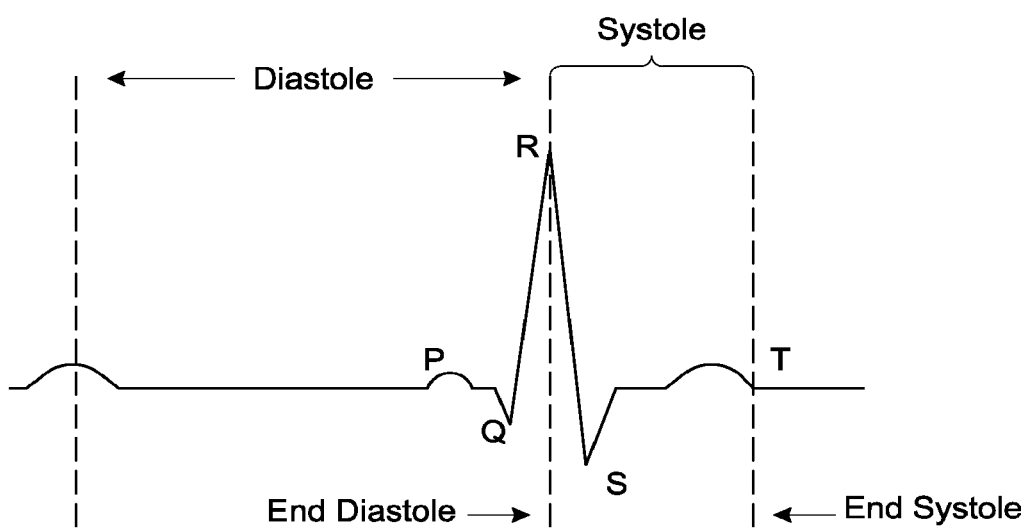
FIG. 4 is a schematic illustration of a surface ECG waveform showing the diastolic and systolic phase.

Post-stent deployment high pressure inflations are performed using the current, standard manual inflation devices. The device described herein may be tied to the transducer that is currently used on every percutaneous coronary intervention to measure intracoronary pressure and/or the standard surface EKG which s currently used on every percutaneous coronary intervention. FIG. 4 shows an example of a surface ECG waveform showing the diastolic and systolic phase.

Figure 5:
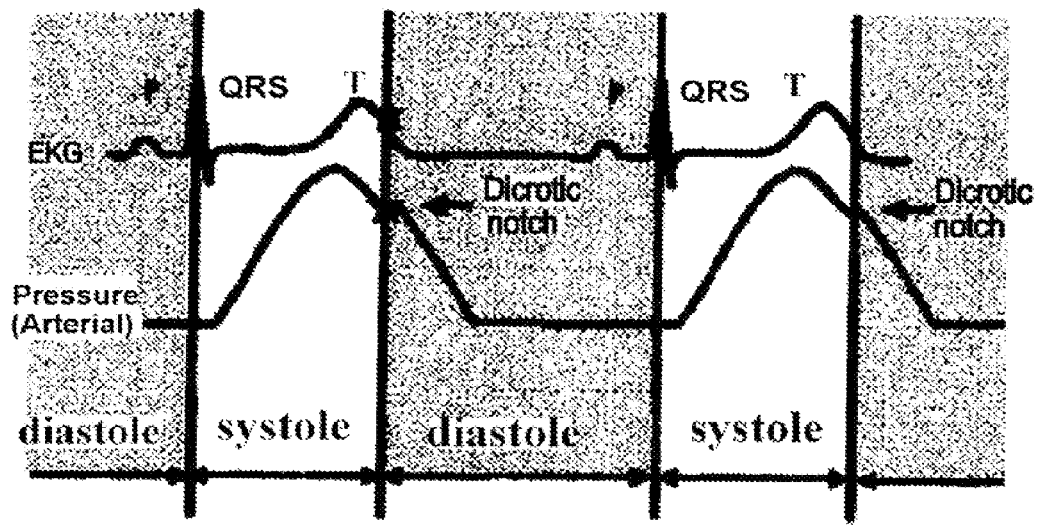
FIG. 5 is a schematic illustration of a simultaneous ECG and coronary arterial pressure recording, indicating the end of the T wave and dicrotic notch indicating the onset of diastole.

FIG. 5 shows simultaneous ECG and coronary arterial pressure recordings indicating the end of the T-wave and dicrotic notch indicating the onset of diastole.

The temporal window for optimal balloon inflation likely occurs at a point within the range of from about 55% to about 85% and in some applications of the invention within the range of from about 65% to about 75%, or at about 70% into the R-R interval. This is during diastole and is the most common motion-free point in the cardiac cycle. This is known from CG gated cardiac CT imaging.

Figure 6:
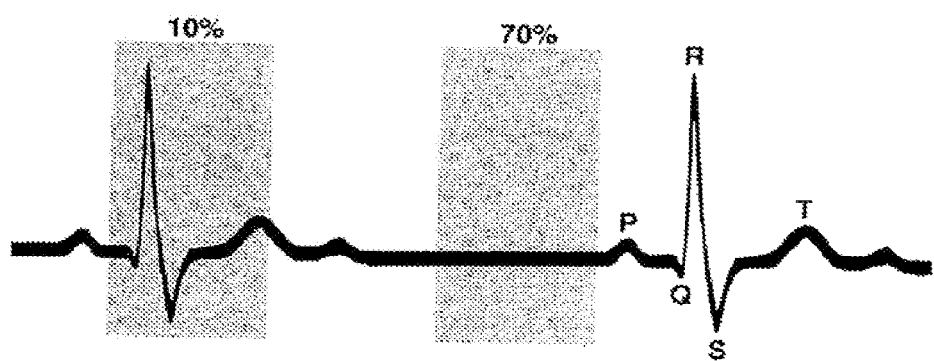
FIG. 6 is a schematic illustration of an ECG, with an inflation target centered at about 70% of the R-R interval.

FIG. 6 shows an ECG with the right box having its center at 70% of the R-R interval and, that the center of the window can be located anywhere during the heart cycle. The left box has its center at 10% of the R-R interval, which is during systole. The right box has its center at 70% of R-R interval, which is during diastole and is most common motion-free imaging temporal window for the heart. On the ECG signal, P represents atrial contraction; Q, R, and S represent ventricular contraction; and T represents ventricular relaxation.

Referring to FIG. 7, there is shown a stent delivery catheter 18 that may be used in accordance with one aspect of the present invention. Although the description below is primarily directed to stent deployment catheters, the catheters disclosed herein may be provided with additional features known in the interventional arts, such as drug delivery, perfusion, RF, cryo or other modality denervation, or any combination of these features, which can be used in combination with the balloon of the present invention as will be readily apparent to one of skill in the art in view of the disclosure herein.

The catheter 18 generally comprises an elongate tubular body 19 extending between a proximal control end 20 and a distal functional end 21. The length of the tubular body 19 depends upon the desired application. For example, lengths in the area of about 130 cm to about 150 cm are typical for use in carotid artery stent deployment by way of a femoral access.

The tubular body 19 may be produced in accordance with any of a variety of known techniques for manufacturing balloon-tipped catheter bodies, such as by extrusion of appropriate biocompatible plastic materials such as HDPE, PEEK and others known in the art. Alternatively, at least a portion or all of the length of tubular body 19 may comprise a spring coil, solid walled hypodermic needle tubing, or braided reinforced wall, as is understood in the catheter and guide wire arts.

In general, tubular body 19, in accordance with the present invention, is provided with a generally circular exterior cross-sectional configuration having an external diameter with the range of from about 0.02 inches to about 0.065 inches. In accordance with one embodiment of the invention, the tubular body 19 has an external diameter of about 0.042 inches (3.2 F) throughout most of its length for use in coronary applications. Alternatively, generally triangular or oval cross-sectional configurations can also be used, as well as other noncircular configurations, depending upon the number of lumen extending through the catheter, the method of manufacture and the intended use.

In a catheter intended for peripheral vascular applications, the tubular body 19 will typically have an outside diameter within the range of from about 0.039 inches to about 0.085 inches. Diameters outside of the preferred ranges may also be used, provided that the functional consequences of the diameter are acceptable for the intended purpose of the catheter. For example, the lower limit of the diameter for tubular body 19 in a given application will be a function of the number of fluid or other functional lumens, desired inflation media infusion rates as will be discussed below, and the desired structural integrity of the catheter.

In general, the dimensions of the catheter shaft and balloon can be optimized by persons of skill in the art in view of the present disclosure to suit any of a wide variety of applications. For example, the balloon of the present invention can be used to deliver stents or other therapeutic functions to large and small arteries and veins, as well as other lumens, potential spaces, hollow organs and surgically created pathways. The present invention may find applicability to a variety of interventions in the esophagus, trachea, urethra, ureters, fallopian tubes, intestines, colon, and any other location accessible by catheter which may benefit from precise timing of a function of the catheter such as dilatation and/or stent delivery, with respect to a biological cycle such as the cardiac cycle or respiratory cycle. This includes surgically created lumens such as, for example, transjugular intrahepatic portosystemic shunts and others which will be recognized by those of skill in the art. Thus, although the present invention will be described herein primarily in terms of arterial bifurcation applications, it is understood that this is for illustrative purposes only, and the present invention may have broader applicability in the field of precision catheter placement and actuation.

Tubular body 19 should have sufficient structural integrity (e.g., "pushability") to permit the catheter to be advanced to a treatment site such as distal arterial locations without buckling or undesirable bending of the tubular body 19. Larger diameters generally have sufficient internal flow properties and structural integrity, but reduce perfusion in the artery in which the catheter is placed. Larger diameter catheter bodies also tend to exhibit reduced flexibility, which can be disadvantageous in applications requiring placement of the distal end of the catheter in a remote vascular location. In addition, lesions requiring treatment are sometimes located in particularly small diameter arteries, necessitating the lowest possible profile.

As illustrated schematically in FIG. 7, the distal end 21 of catheter 18 is provided with at least one inflatable balloon 26. The proximal end 20 of catheter 18 is provided with a manifold 23 which may have one or more access ports, as is known in the art. Generally, manifold 23 is provided with a guide wire port 24 in an over the wire embodiment and a balloon inflation port 25. Additional access ports are provided as needed, depending upon the functional capabilities of the catheter 18.

The balloon 26 can also alternatively be mounted on a rapid exchange type catheter, in which the proximal guidewire port 24 would not appear on the manifold 23 as is understood in the art. In a rapid exchange embodiment, the proximal guidewire access port 24 is positioned along the length of the tubular body 19, such as between about 1 and about 20 cm and typically between about 10 cm and 20 cm from the distal end of the catheter. See FIG. 8.

The proximal guidewire access port 24 is in communication with distal guidewire access port 32 by way of a guidewire lumen 28. Inflation lumen 30 places the proximal inflation port 25 in communication with the balloon 26. The catheter may be provided with one or two or more radiopaque markers 34, to facilitate visualization of the balloon.

The balloon 26 may have a generally cylindrical inflated profile throughout its axial working length such as with conventional PTCA balloons. The overall dimensions of any particular balloon 26 will be governed by the intended use, as will be well understood to those of ordinary skill in the art. For example, balloons can be inflatable to a diameter of anywhere within the range of from about 1.5 mm to about 10 mm. For coronary vascular applications, the balloon 26 will normally be inflatable to a diameter within the range of from about 1.5 mm to about 4 mm, with balloons available at about every 0.25 mm increment in between. In one particular noncompliant balloon design (PET balloon, having a wall thickness of about 0.0006 to about 0.0008 inches) at an inflation pressure of about 8 atmospheres, the balloon has an outside diameter of about about 3.4 mm. The same balloon at 18 atmospheres inflation pressure may have an outside diameter of about 3.5 mm. Alternative, compliant material balloons will exhibit a greater expansion as a function of inflation pressure as is understood in the art.

The axial length of the balloon can be varied considerably, depending upon the desired functionality as is understood. For example, the axial length of the working section of the balloon may be anywhere within the range of from about 0.5 cm to about 5.0 cm or longer. For coronary vascular applications, the axial length of the working section will normally be within the range of from about 0.5 cm to about 2.0 cm. Other features and considerations for dilatation and stent delivery balloons are well understood and will not be detailed further herein.

As has been discussed above, the present invention permits inflation of the balloon such that full or substantially full inflation is reached at a precise point, relative to an anatomical cycle such as the cardiac cycle. This enables fixation of the location of a stent at a precise, predetermined point. Inflation may be accomplished over a length of time that exceeds a single cardiac cycle, with the completion of inflation/fixation occurring at the predetermined point in the cardiac cycle. Alternatively, inflation may be accomplished rapidly within a single diastolic cycle, as has been discussed.

The foregoing is accomplished by providing a signal source, from which a drive signal can be derived which is indicative of the cardiac cycle. The drive signal may be utilized to either control a pump function, or control the flow of inflation media from a pump into or through the catheter, in order to accomplish the completion of the inflation cycle at the predetermined point.

Figure 10:
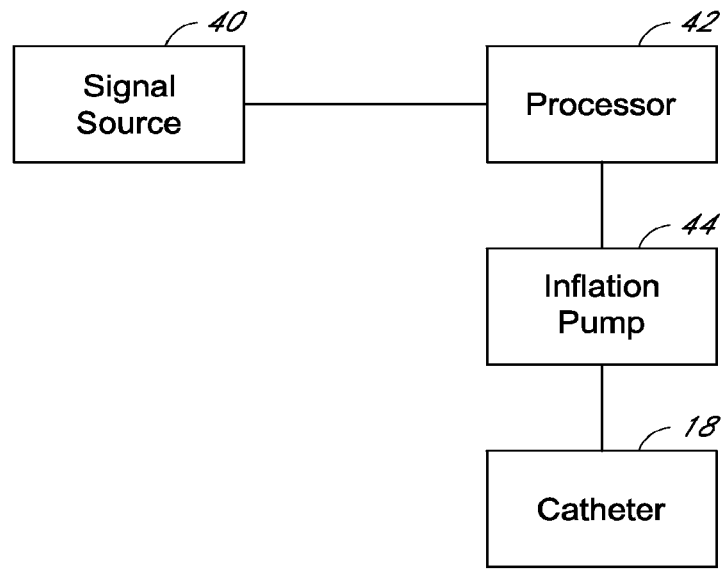
FIG. 10 is a schematic block diagram of a precision stent deployment system, having a signal processor controlled inflation pump.

Referring to FIG. 10, the signal source 40 may be any of a variety of devices currently used during percutaneous coronary intervention to measure intracoronary pressure, as previously described. A drive signal from the processor 42 is directed to an inflation pump 44, to inflate the catheter 18. Inflation pump 44 may be activated by the drive signal to inflate the catheter in either a slow continuous inflation cycle, a single abrupt inflation within a single diastolic cyclic, or pulsitile inflation configuration. The processor 42 may include software for extracting or deriving an appropriate drive signal from the signal source 40.

Figure 11:
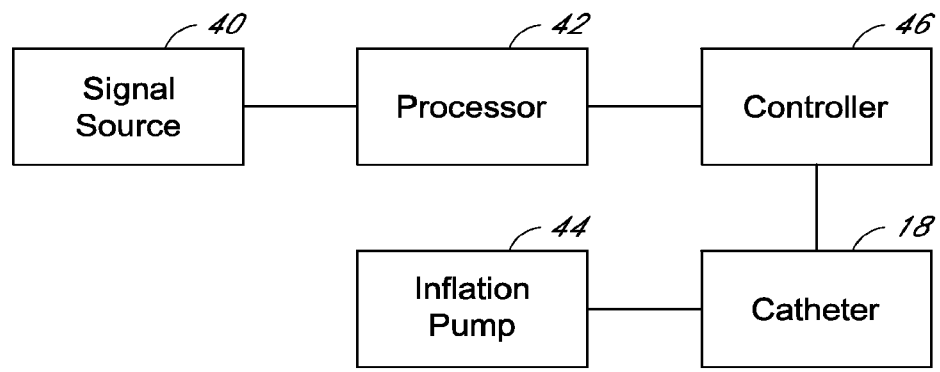
FIG. 11 is a schematic block diagram of an alternate precision stent deployment system, having a microprocessor controlled flow regulator between the output of an inflation pump and the inflatable balloon.

Alternatively, referring to FIG. 11, the output from the signal source 40 and processor 42 is coupled directly to the catheter 18 or to a control unit 46 between the inflation pump 44 and the catheter 18. In this implementation of the invention, inflation pump 44 may be activated, such as electronically, or by complete depression of a manual pump such as an Indeflator, Digiflator, or other common disposable or reusable inflation system.

The controller 46 comprises a variable valve, such as a variable aperture or other structure for controllably reducing the flow rate from the inflation pump 44 to the catheter 18. In this implementation of the invention, the physician can fully depress the plunger or otherwise activate the pump, and allow the system to automatically restrict inflation of the catheter to a predetermined ramp which achieves stent placement at the predesired point in the diastolic cycle which corresponds to the desired physical target location for the stent. This implementation of the invention permits at least the processor 42 and associated electronics to be positioned outside of the sterile field for reuse. The control can be either a reusable component or a one-time use disposable component.

In order to achieve full expansion of the stent at a precise target such as 70%.+−0.5% or 10% into the R-R interval, balloon inflation lumen diameter, balloon volume, catheter length and inflation media viscosity may desirably be taken into account. The processor 40 may be provided with electronics to calibrate the system to each of one or two or three or more different commercially available angioplasty catheters. Alternatively, a unique angioplasty catheter may be provided which is precalibrated for use in the present system, to enable precise achievement of the inflation end point.

Utilization of a control 46 which limits inflation rate may allow the driving system of the present invention to be coupled to any of a variety of commercially available angioplasty catheters, and allow achievement of the inflation target point, since the control can reduce the inflation rate (with a correspondingly earlier commencement of the inflation window) below the maximum inflation rate of the "slowest" available catheter.

In an implementation of the invention intended for a single burst inflation within a single diastolic cycle, any of a variety of factors may be modified on conventional angioplasty catheters to enable rapid inflation rates. For example, the inside diameter of the inflation lumen may be increased either by reducing the wall thickness of the catheter, and/or increasing the outer diameter of the catheter proximal to the balloon. Inflation rates may be increased by reducing the viscosity of the inflation media, including switching to a gas such as $Co2$ or helium.

Systems in accordance with the present invention can be constructed in any of a variety of ways, such as to enable use of commercially available angioplasty catheters, commercially available inflation pumps, or a variety of combinations of specialized pumps or catheters.

Figure 12:
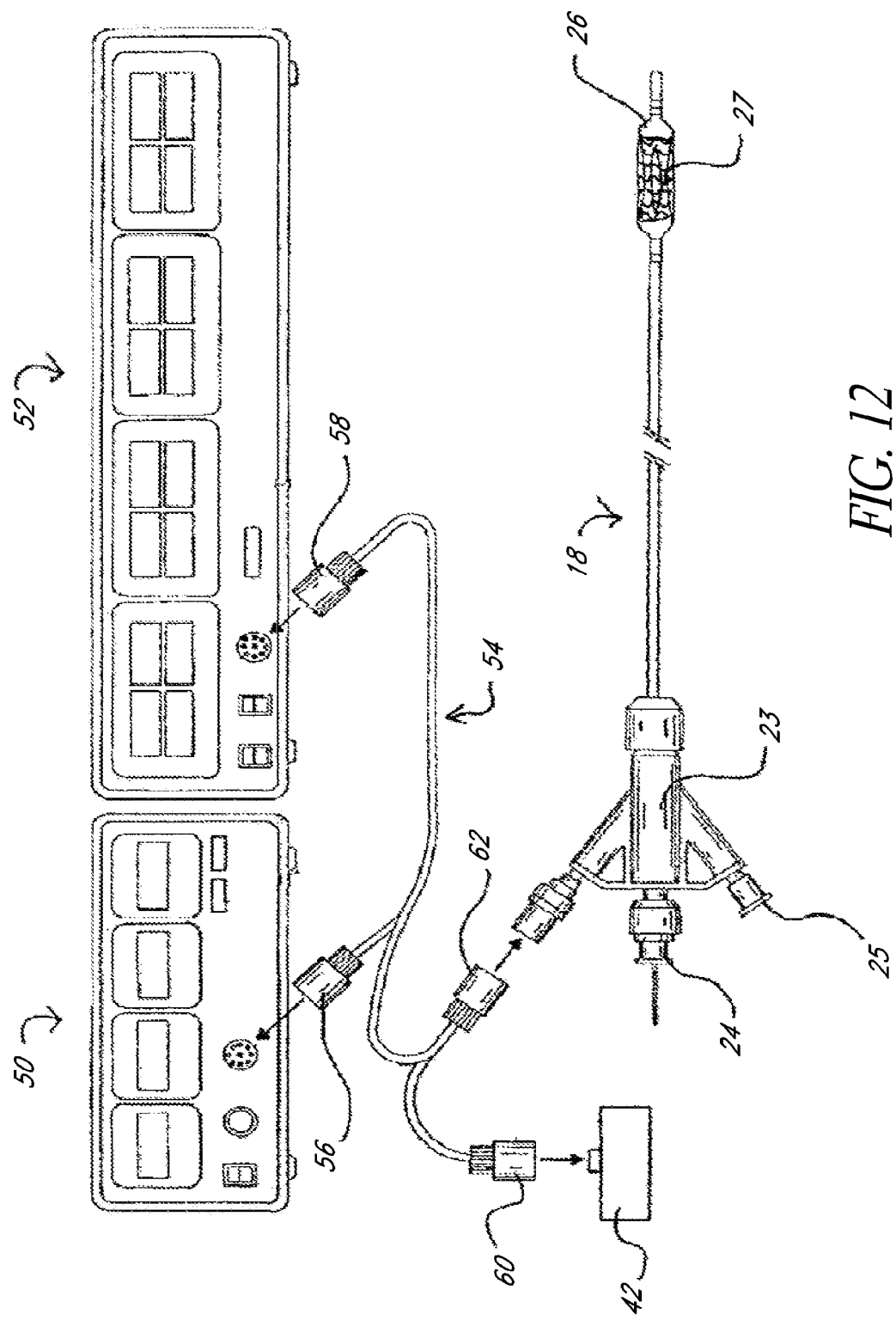
FIG. 12 is a schematic view of a system including a cable set, balloon catheter, processor and standard cath lab instrumentation capable of generating a signal indicative of the cardiac cycle.

Referring to FIG. 12, there is illustrated one example system in which a specialized catheter including a flow regulator therein is coupled to a conventional inflation pump and standard electronics found in the cath lab. As illustrated therein, a first signal source 50 comprises a standard piece of cath lab instrumentation which is capable of generating a signal indicative of the cardiac cycle. A second signal source 52 may be a different type of electronic equipment available in cath labs, which is also capable of generating a signal indicative of the cardiac cycle. A cable set 54 may be provided with a first connector 56 adapted to connect to the first signal source 50. Optionally, the cable set 54 may be provided with a second connector 58 which may be adapted to connect to the second signal source 52. In a given clinical environment, one or the other of the signal sources 50 or 52 may be unavailable, or otherwise more or less desirable for use in the operation of the present system.

Cable set 54 may be provided with a connector 60, for connecting to a processor 42 as has been discussed. Processor 42 is responsible for adapting the signal from the first signal source 50 or second signal source 52 into a drive signal, for driving the pressure regulator. Cable set 54 may additionally be provided with a connector 62, for placing the cable set 54 into electrical communication with a manifold 23 on catheter 18. Manifold 23 may be provided with an internal flow regulator, responsive to a signal received from the cable set 54, for regulating the pressure and/or flow rate of inflation media from inflation port 25 via catheter 18 to the balloon 26. Manifold 23 is illustrated as comprising a proximal guidewire port 24, which will be present in an over the wire catheter configuration as is understood in the art. Guidewire port 24 will be omitted from the manifold 23 in a rapid exchange configuration.

The manifold 23 is further provided with an inflation port 25, for coupling to a conventional source of pressurized inflation media.

In the foregoing configuration, the clinician may fully depress the piston or lever on an inflation device, applying full pressure to the inflation port 25. The flow regulator within manifold 23, controlled by the signal received from processor 42 will adjust the regulator to achieve an inflation rate which achieves balloon dilation at the predetermined point within the cardiac cycle, thereby enabling deployment of the stent 27 at the precise, predetermined target location within the vasculature.

Although the present invention has been described in terms of certain preferred embodiments, it may be incorporated into other embodiments by persons of skill in the art in view of the disclosure herein. The scope of the invention is therefore not intended to be limited by the specific embodiments disclosed herein.

What is claimed:

1. A control system for controlling an inflation of a balloon in a balloon stent catheter arrangement, comprising, (i) a transducer adapted to receive a source of intracoronary arterial pressure in a patient's coronary artery and to provide an arterial pressure waveform data indicative of a status of the patient's cardiac cycle based upon the source of intracoronary arterial pressure, (ii) a processing system adapted to process the arterial pressure waveform data and to provide a control signal based on the arterial pressure waveform data for inflating the balloon in diastole; and (iii) an inflation pump adapted to inflate the balloon, the processing system being adapted to cause the inflation pump to inflate the balloon in diastole, corresponding to about 55% to about 85% of a single R-R interval of the patient's cardiac cycle, by an amount sufficient to achieve fixation of a stent in the balloon stent catheter arrangement at a target site in the patient's coronary artery.

2. The control system according to claim 1 further comprising a guiding element adapted to provide the source of intracoronary arterial pressure at a distal end thereof.

3. The control system according to claim 1 further comprising a guiding element, the source of intracoronary arterial pressure being disposed on the guiding element.

4. The control system of claim 1 wherein the processing system is adapted to cause the balloon to inflate sufficiently to achieve fixation of the stent within 1 mm of the target site.

5. The control system of claim 1 wherein the processing system is adapted to cause the balloon to substantially fully inflate during a single diastole.

6. The control system of claim 1 wherein the processing system is adapted to cause the balloon to inflate over a time period that exceeds a single cardiac cycle.

7. The control system according to claim 1 wherein the processing system is adapted to adjust an inflation rate of the balloon for a given inflation pressure circumstance.

8. The control system according to claim 1 wherein the processing system is adapted to determine when to begin inflation of the balloon so as to achieve fixation of the stent at the target site.

9. The control system of claim 1 wherein the processing system is adapted to cause the balloon to inflate in a continuous inflation cycle.

10. The control system of claim 1 wherein the processing system is adapted to cause the balloon to inflate in a pulsatile manner.

* * * * *